US00PP31391P2

(12) United States Plant Patent
van Langen

(10) Patent No.: US PP31,391 P2
(45) Date of Patent: Jan. 21, 2020

(54) ***ECHEVERIA* PLANT NAMED 'AMIECH1822'**

(50) Latin Name: ***Echeveria* hybrid**
Varietal Denomination: AMIECH1822

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 16/350,413

(22) Filed: Nov. 13, 2018

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373, 263.1
CPC ... A01H 5/12; A01H 5/02; A01H 5/00; A01H 6/32; A01H 6/00
See application file for complete search history.

*Primary Examiner* — June Hwu
(74) *Attorney, Agent, or Firm* — Samuel R. McCoy, Jr.

(57) ABSTRACT

A new and distinct *Echeveria* cultivar named 'AMIECH1822' which is characterized by a short plant height, strong foliage, light greyed-green foliage with a bluish hue, and foliage which is margined greyed-red at and near the apex. The new variety has shown to be uniform and stable in the resulting generations from asexual propagation.

3 Drawing Sheets

Latin name of the genus and species: The Latin name of the genus and species of the novel variety disclosed herein is *Echeveria* hybrid.

Variety denomination: The inventive variety of *Echeveria* disclosed herein has been given the variety denomination 'AMIECH1822'.

BACKGROUND OF THE INVENTION

Parentage: 'AMIECH1822' is a seedling selection resulting from the controlled pollination of an unnamed and unpatented *Echeveria elegans* plant, the seed parent, with and unpatented, proprietary pollen parent referred to as *Echeveria* hybrid 'E120041'. The crossing was made by the inventor in the summer of 2011 at a commercial greenhouse in Heerhugowaard, the Netherlands. One seedling resulting from said cross was observed to exhibit unique growth and foliage characteristics and was isolated for further evaluation in order to confirm the distinctness and stability of the characteristics first observed. Upon confirmation of distinctness and stability, 'AMIECH1822' was selected for commercialization in the spring of 2013.

Asexual Reproduction: Asexual reproduction of the new cultivar 'AMIECH1822', by way of rooting leaf cuttings, was first initiated in the summer of 2014 at the inventor's commercial greenhouse in Heerhugowaard, the Netherlands. Through four subsequent generations, the unique features of this cultivar have proven to be stable and true to type.

SUMMARY OF THE INVENTION

The cultivar 'AMIECH1822' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH1822'. These characteristics in combination distinguish 'AMIECH1822' as a new and distinct *Echeveria* cultivar:

1. 'AMIECH1822' exhibits a very compact rosette of thick, strong foliage; and
2. 'AMIECH1822' exhibits very light greyed-green, glaucous juvenile foliage with a bluish hue; and
3. 'AMIECH1822' exhibits glaucous greyed-green mature foliage, with a bluish hue, and greyed-red margins at and near the apex.

BOTANICAL DESCRIPTION OF THE PLANT

Figure 1:
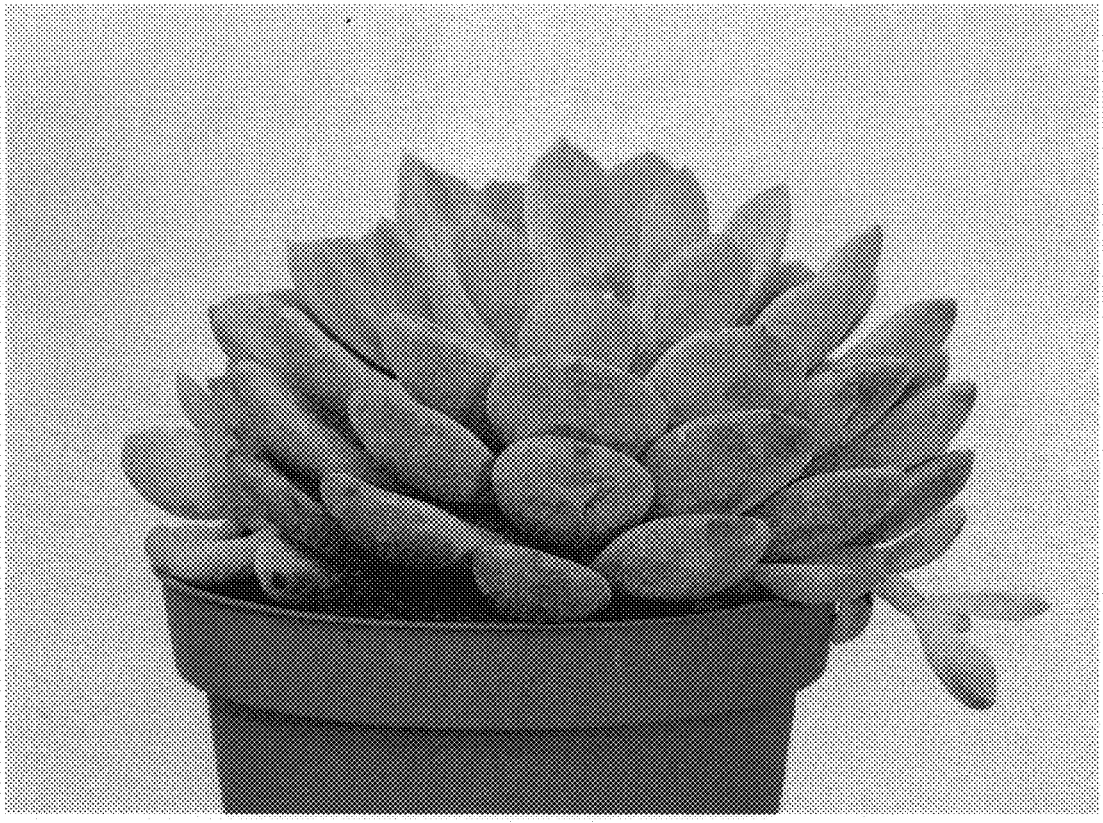
FIG. 1 illustrates, as nearly true as it is reasonably possible to make the same in color photographs of this type, an exemplary plant of 'AMIECH1822' grown in a commercial greenhouse in Heerhugowaard, the Netherlands. This plant is approximately 7 months old, shown planted in a 10 cm container.
Figure 2:
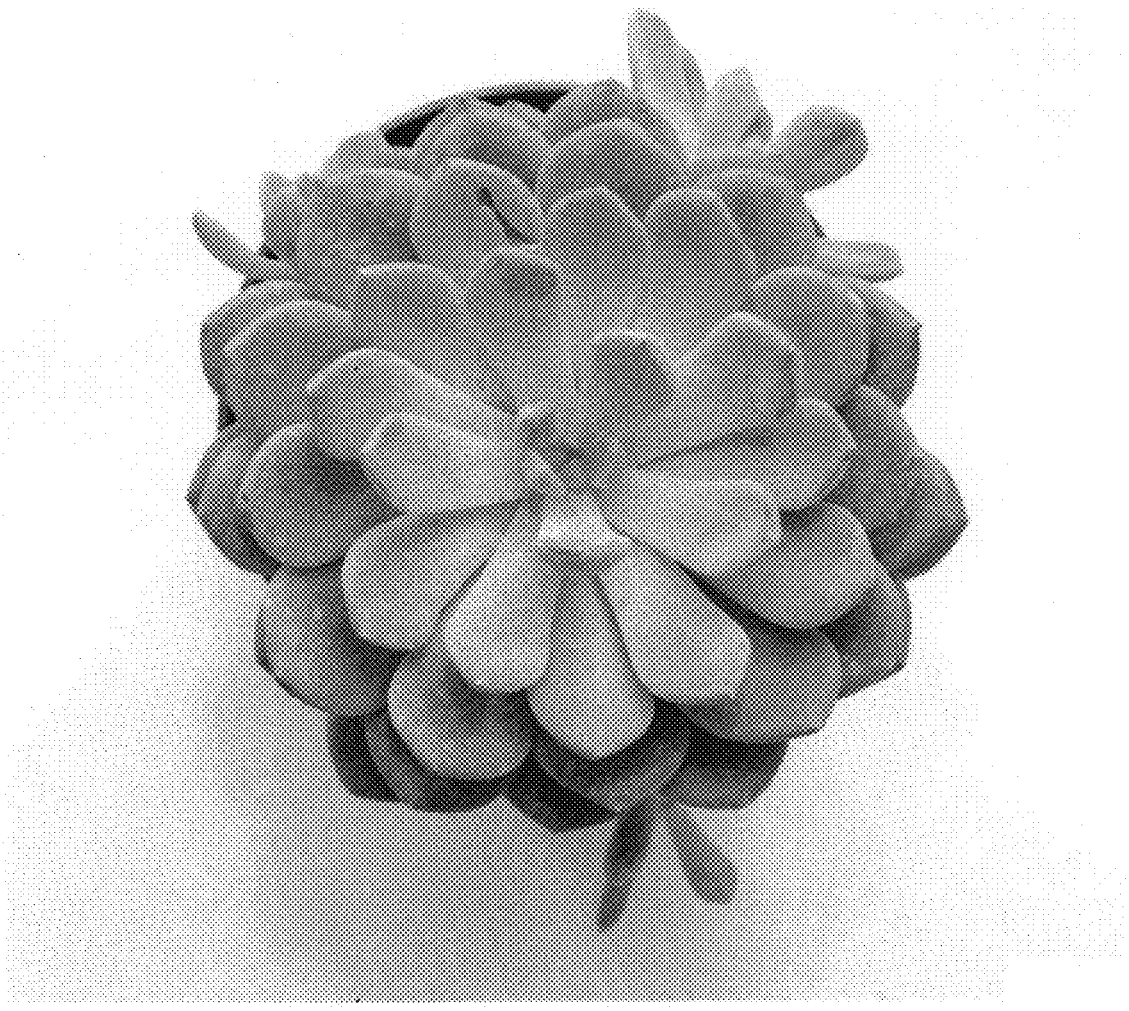
FIG. 2 illustrates, as nearly true as it is reasonably possible to make the same in color photographs of this type, the typical foliage arrangement of 'AMIECH1822'.
Figure 3:
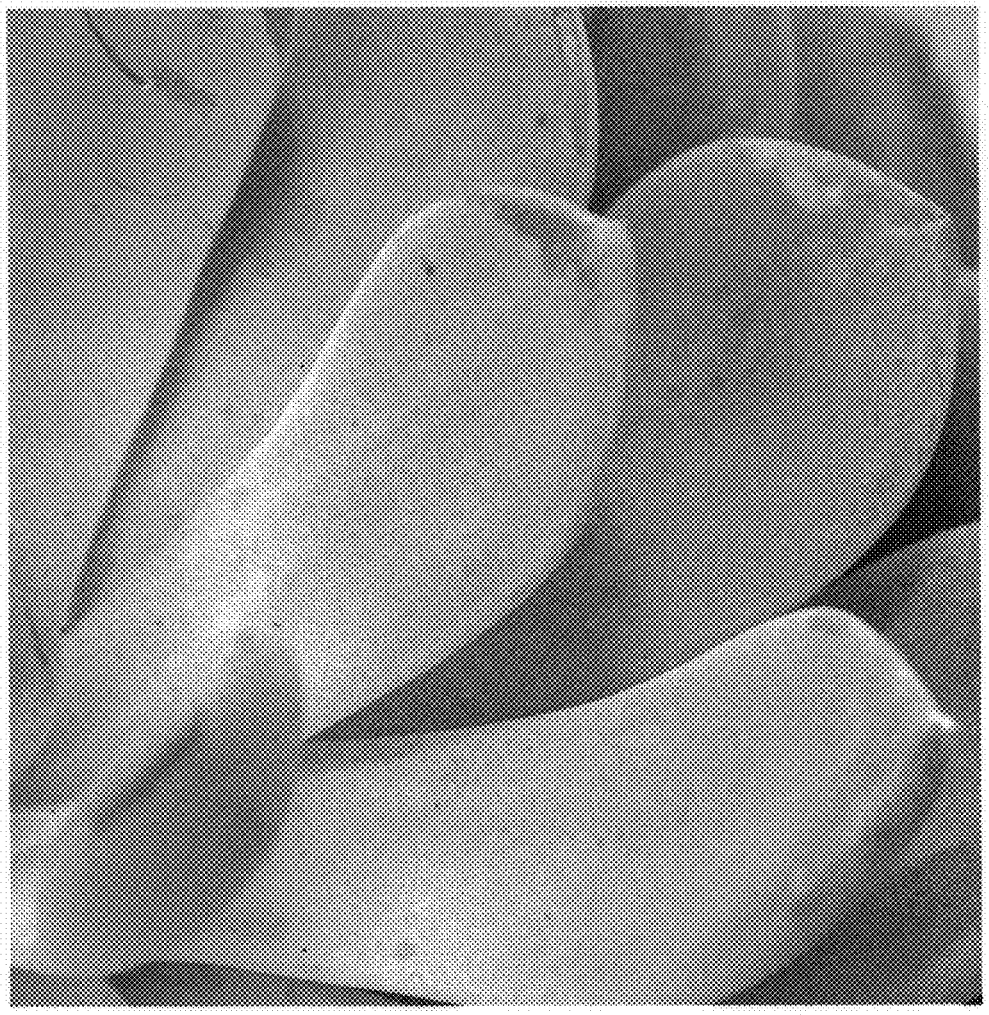
FIG. 3 illustrates, as nearly true as it is reasonably possible to make the same in color photographs of this type, the mature foliage 'AMIECH1822'.

The following observations and measurements made in November of 2016 describe averages from a sample set of six specimens of 7 months old 'AMIECH1822' plants grown in 10 cm nursery containers at commercial greenhouse in Heerhugowaard, the Netherlands. Plants were produced using conventional greenhouse production protocols for *Echeveria* which consisted of minimal irrigation and fertilizer applications, and chemical pest and disease control measures against mealy bug as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH1822' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIECH1822' and comparisons with the parents and closest known comparator are provided below.

Plant description:

*Growth habit*.—Succulent perennial with foliage growing in a basal rosette.

*Plant profile*.—Flattened globular.

*Height from soil level to top of foliar plane*.—7.0 cm.

*Plant spread*.—Average of 20.0 cm.

*Growth rate*.—Moderate.

*Plant vigor*.—Moderately vigorous.

*Propagation*.—Type — Leaf cuttings. Time to initiate rooting — Approximately 21 to 35 days at an approximate temperature of 18 degrees Celsius. Crop time — Approximately 18 to 22 weeks to produce a marketable plant in a 7 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a basal rosettes, with lateral branches growing from the base.

*Quantity of lateral branches*.—3.

*Dimensions*.—4.3 cm long and 0.7 cm in diameter.

*Internode length*.—0.2 cm.

*Cross section*.—Rounded.

*Aspect*.—Nearly horizontal.

*Strength*.—Moderately strong.

*Texture and luster*.—Glabrous and matte.

*Color when developing*.—Yellow-green, nearest to RHS 145D.

*Mature color*.—Yellow-green, nearest to RHS 145D.

*Color at internodes*.—Yellow-green, nearest to RHS 145D.

Foliage:

*Arrangement*.—Rosette.

*Division*.—Simple.

*Attachment*.—Sessile.

*Quantity*.—Approximately 58 leaves per rosette.

*Shape*.—Thick, succulent leaves which are obovate to spatulate.

*Dimensions*.—5.3 cm long, 2.4 cm wide, and 0.5 cm thick, on average.

*Aspect*.—Slightly concave and slightly curved upward toward the distal end.

*Attitude*.—Younger foliage near the center of the rosette is very upright; foliage becoming progressively more relaxed towards the outer whorl of the rosette, at an angle of approximately 30 degrees to horizontal.

*Apex*.—Short apiculate.

*Base*.—Long cuneate.

*Margin*.—Entire; not undulated or lobed.

*Pubescence, texture and luster of the adaxial surface*.—Glabrous, smooth, and matte; moderately glaucous.

*Pubescence, texture and luster of the abaxial surface*.—Glabrous, smooth, and matte; moderately glaucous.

*Color*.—Juvenile foliage, adaxial surface — Greyed-green, nearest to RHS 191A, and fading lighter towards the base, nearest to RHS 193A. The epicuticular glaucous wax covering the leaf surface is greyed-green, nearest to RHS 188A. Juvenile foliage, abaxial surface — Greyed-green, nearest to RHS 191B, and fading lighter towards the base, nearest to RHS 193A. The epicuticular glaucous wax covering the leaf surface is greyed-green, nearest to RHS 188A. Mature foliage, adaxial surface — In between yellow-green and greyed- green, RHS 147B and 191A, and fading lighter towards the base, nearest to a mixture of RHS 147C and 147D; margins towards and at the apex are strongly suffused with greyed-red, RHS 182C. The epicuticular glaucous wax covering the leaf surface is greyed-green, nearest to RHS 188A. Mature foliage, abaxial surface — Green, nearest to RHS 138B, and becoming greyed-green towards the base, nearest to RHS 193A; margins are greyed-red, in between RHS 180A and 180B. The epicuticular glaucous wax covering the leaf surface is greyed-green, nearest to RHS 188A.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'AMIECH1822' differ from the seed parent, an unnamed *Echeveria elegans* plant (not patented), in the following characteristics described in Table 1 below.

TABLE 1

| Characteristic | 'AMIECH1822' | Seed parent |
|---|---|---|
| Foliage apex. | Short apiculate. | Mucronate. |
| Foliage cross-section. | More rounded than the seed parent. | Flatter than 'AMIECH1822'. |
| Foliage strength. | Stronger than the seed parent. | Weaker than 'AMIECH1822'. |
| General coloration of the mature foliage. | Greyed-green and margined greyed-red towards and at the apex. | Greyed-green. |

The pollen parent, *Echeveria* hybrid 'E120041' (not patented), is no longer in cultivation or otherwise available, therefore a comparison is not possible.

COMPARISONS WITH THE CLOSEST KNOWN COMMERCIAL COMPARATOR

Plants of the new cultivar 'AMIECH1822' differ from the most similar commercial variety known to the inventor, *Echeveria elegans* 'Blue' (not patented), in the following characteristics described in Table 2 below.

TABLE 2

| Characteristic | 'AMIECH1822' | 'Blue' |
|---|---|---|
| Plant profile. | Flattened globular. | Upright globular. |
| Foliage length. | Shorter than 'Blue'. | Longer than 'AMIECH1822'. |
| Foliage apex. | Short apiculate. | Obtuse. |
| Foliage cross-section. | Flatter than 'Blue'. | More rounded than 'AMIECH1822'. |
| General coloration of the mature foliage. | Light greyed-green and margined greyed-red towards and at the apex. | Blue-grey. |

That which is claimed is:

1. A new and distinct variety of *Echeveria* plant named 'AMIECH1822', substantially as described and illustrated herein.

* * * * *